United States Patent [19]

Cohnen

[11] 4,265,903
[45] May 5, 1981

[54] ARYL-SUBSTITUTED FURNACES

[75] Inventor: Erich Cohnen, Hamburg, Fed. Rep. of Germany

[73] Assignee: Beiersdorf Aktiengesellschaft, Hamburg, Fed. Rep. of Germany

[21] Appl. No.: 135,954

[22] Filed: Mar. 31, 1980

[30] Foreign Application Priority Data

Apr. 7, 1979 [DE] Fed. Rep. of Germany ....... 2914166

[51] Int. Cl.$^3$ .................... A61K 31/34; C07D 307/42; C07D 307/54
[52] U.S. Cl. ............................ 424/282; 260/340.5 R; 260/347.3; 260/347.7; 260/347.8; 260/348.15; 260/348.46; 260/348.48; 260/348.63; 424/285
[58] Field of Search .......... 260/347.3, 347.7, 340.5 R; 424/282, 285

[56] References Cited

U.S. PATENT DOCUMENTS 3,723,476 3/1973 Nakanishi et al. ................. 260/347.7
4,115,409 9/1978 Large ............................... 260/347.7

Primary Examiner—Richard Raymond
Attorney, Agent, or Firm—Bierman & Bierman

[57] ABSTRACT

Aryl substituted furnaces and pharmaceutically acceptable acid addition salts thereof according to the following formula

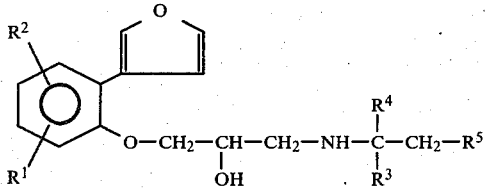

wherein $R_1$ and $R_2$ may be the same or different and are selected from hydrogen, halogen, alkyl and acylamino having 1 to 4 carbon atoms, $R_3$ and $R_4$ may be the same or different and are selected from hydrogen and methyl, $R_5$ is selected from hydrogen, dimethoxyphenyl and acylamino having the following formula

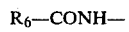

wherein $R_6$ is selected from alkyl having 1 to 4 carbon atoms, are disclosed which are useful as anti-hypertensive and β-adrenolytic agents. Also, substituted furnaces having the formula

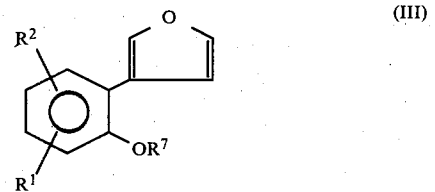

wherein $R_7$ is selected from hydrogen, benzyl, the radical

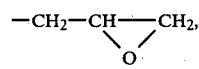

and the radical

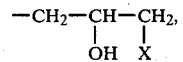

wherein X is selected from chlorine and bromine, are disclosed which are useful in the preparation of the aryl substituted furnaces. Compositions containing the aryl substituted furnaces, and methods of preparation are also disclosed.

7 Claims, No Drawings

ARYL-SUBSTITUTED FURANCES

BACKGROUND OF THE INVENTION

The invention relates to aryl substituted furanes and their pharmaceutically acceptable acid addition salts which are useful as β-adrenolytic and anti hypertensive agents. Compositions containing said compounds, their method of use, and methods of preparation form a part of the present invention, along with novel substituted furanes useful in the preparation of said aryl-substituted furanes. The entire specification and claims of application Ser. No. 57,050, filed June 17, 1979, is incorporated herein by reference.

SUMMARY OF THE INVENTION

The aryl substituted furanes according to the present invention are represented by the following formula.

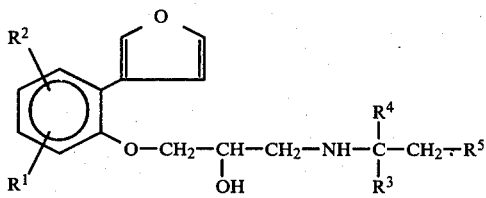

wherein $R_1$ and $R_2$ may be the same or different and are selected from hydrogen, halogen, alkyl and acylamino having 1 to 4 carbon atoms, $R_3$ and $R_4$ may be the same or different and are selected from hydrogen and methyl, $R_5$ is selected from hydrogen, dimethoxyphenyl and acylamino having the following formula

wherein $R_6$ is selected from alkyl having 1 to 4 carbon atoms.

Particularly preferred aryl substituted furanes of the present invention are selected from 3-[2-(2-hydroxy-3-tertiarybutylamino-propoxy)-phenyl]-furane, 3-[2-(2-hydroxy-3-isopropylamino-propoxy)-phenyl]-furane, 3-[2-(2-hydroxy-3-tertiarybutylamino-propoxy)-4-methyl-phenyl]-furane, 3-[2-(2-hydroxy-3-tertiarybutylamino-propoxy)-5-methyl-phenyl]-furane, 3-[2-(2-hydroxy-3-tertiarybutylamino-propoxy)-4-(n-propyl)-phenyl]-furane, 3-[2-(2-hydroxy-3-tertiarybutylamino-propoxy)-5-(n-propyl)-phenyl]-furane, 3-[2-(2-hydroxy-3-tertiarybutylamino-propoxy)-4,5-dimethylphenyl]-furane, 3-[2-(2-hydroxy-3-tertiarybutylamino-propoxy)-4-chlorophenyl]-furane, 3-[2-(2-hydroxy-3-tertiarybutylamino-propoxy)-5-acetamidophenyl]-furane, 3-[2-(2-hydroxy-3-[3,4-dimethoxyphenyl]-ethylamino-propoxy)-phenyl]-furane, 3-[2-(2-hydroxy-3-acetamidoethylamino-propoxy)-phenyl]-furane, and 3-[2-(2-hydroxy-3-isopropionamido-ethylamino-propoxy)-phenyl]-furane.

The compounds encompassed by formula I are also useful in the form of acid addition salts. The salts can be prepared by reacting the compounds with suitable organic or inorganic acids. Preferred organic acids include oxalic acid, fumaric acid and maleic acid. Preferred inorganic acids include the halogen hydracids, such as, for example, HCl and HBr, and sulfuric acid. More specifically, an organic solvent solution of the compound is mixed with an alcohol solution of the desired acid.

Compositions of the present compounds can be readily prepared by combining the compounds or the respective pharmaceutically acceptable acid addition salts with a pharmaceutically acceptable solid or liquid carrier. Particularly preferred carriers are selected from lactose, gelatin, cornstarch, stearic acid, ethanol, propylene glycol, ethers of tetrahydrofurfuryl alcohol and water.

The compounds and compositions presently contemplated may be administered to a warm blooded animal in the form of solutions for injection. Particularly preferred is peroral administration in the form of dragees, pills or tablets. Peroral administration for humans may range in dosage from 10 to 200 milligrams per day. The present compounds and compositions exhibit β-adrenolytic and blood pressure lowering action and can be employed for the treatment of angina pectoris, hypertonia and arrhythmia.

The present invention also relates to substituted furanes represented by the formula

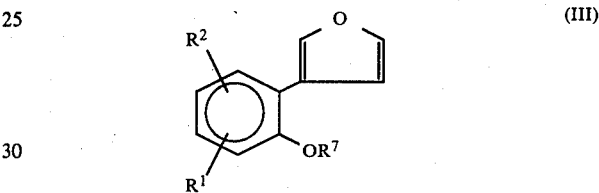

wherein $R_1$ and $R_2$ are as described in formula I, and wherein $R_7$ is selected from hydrogen, a benzyl group, the radical

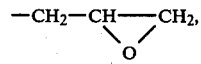

and the radical

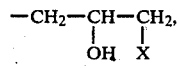

wherein X is selected from chlorine and bromine. When the compound of formula III is prepared wherein $R_7$ is either the radical

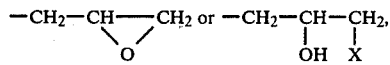

the compounds are formed which are represented by the following formulas

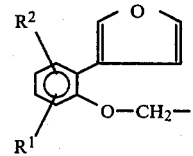
(IV)

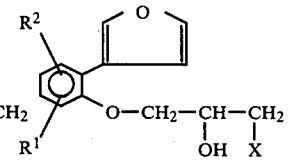
(V)

wherein $R_1$, $R_2$, and X are as previously described with reference to formula III.

The compounds of formulas IV and V are useful in the method of preparing the compounds of formula I. Specifically, the compounds of formula IV and V, either alone or in mixture with each other, are reacted with an amine of the formula

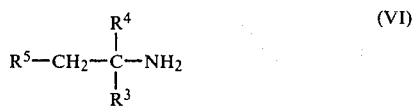

wherein $R_3$, $R_4$ and $R_5$ are as described in formula I. An excess of the amine reactant is preferably employed, and the reaction is carried out in the presence of an alcohol such as tertiary butanol, and at a temperature of from 20° to 60° C. Preferably, the reaction is conducted at room temperature under mild agitation, as by stirring, for up to as long as two days. After isolation, the resulting reaction product may be converted to the acid salt by treatment with an alcoholic solution of one of the acids stated earlier as suitable for this purpose.

In particular, the substituted furanes of the present invention defined by formula III are selected from 3-(2-benzyloxy phenyl)-furane, 3-(2-benzyloxy-4-methyl-phenyl)-furane, 3-(2-benzyloxy-4-n-propyl phenyl)-furane, 3-(2-benzyloxy-5-n-propyl phenyl)-furane, 3-(2-benzyloxy-4-chlorophenyl)-furane, 3-(2-benzyloxy-5-acetamidophenyl)-furane, 3-(2-benzyloxy-4,5-dimethyl-phenyl)-furane, 3-(2-hydroxyphenyl)-furane, 3-[2-(2,3-epoxy-propoxy)-phenyl-]-furane, and the hydroxyhalopropoxyphenyl furanes comprising 3-[2-(2-hydroxy-3-chloropropoxy)-phenyl]-furane and 3-[2-(2-hydroxy-3-bromopropoxy)-phenyl]-furane.

As noted earlier, the compounds according to formula III have utility in the preparation of the arylsubstituted furanes of the present invention. Particularly, the epoxy-propoxy phenyl substituted furane, comprising the compound of formula IV, and the hydroxyhalopropoxy phenyl furanes of formula V have been discussed above as reactants in the final step of the preparation of the compounds of the present invention. Additionally, the compounds of formulas IV and V are prepared from compounds according to formula III wherein $R_7$ is hydrogen. The hydroxy phenyl furanes comprise phenols that are obtainable from the corresponding benzyl ethers of formula III wherein $R_7$ is a benzyl group.

The compounds of formula III can be prepared according to the methods described below. In order to prepare compounds of formula III wherein $R_1$ and $R_2$ are as previously described in formula I and $R_7$ is a benzyl group, compounds having the formula

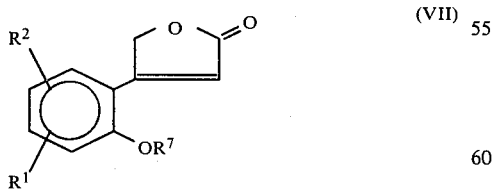

wherein $R_1$ and $R_2$ are as described in formula I and $R_7$ is a benzyl group, are reduced with di-isobutyl aluminum hydride (DIBAH) by the method of Minato and Nagasaki, reported in Chem. Ind. (1965), page 899. More particularly, the above-mentioned 4-aryl-2,5-dihydro-furane-2-ones of formula VII are placed in a tetrahydrofurane solution, and held in a reducing atmosphere at a lowered temperature such as −60° C. DIBAH is an organic solvent such as toluene, is added dropwise to the furane-one solution and the resulting reaction mixture is stirred at the same temperature for a period of time such as 30 minutes. Excess DIBAH is decomposed by the addition of 6N HCl after which the reaction mixture is poured onto ice water and extracted with chloroform. The furane product is finally isolated after evaporation of the solvent.

The benzyl ethers such as prepared by the above method, may then be transformed into the corresponding phenols by hydrogenation with hydrogen at a temperature such as room temperature, in the presence of precious metal catalysts such as palladium/activated carbon. The phenols comprising those compounds of formula III in which $R_7$ is hydrogen, are very unstable compounds. Therefore, immediately after the preparation of these compounds by hydrogenation, they should be reacted with either epichlorohydrin or epibromohydrin to convert them to the compounds of formulas IV and V. In this reaction, compounds IV and V are obtained as mixtures which may be separated by column chromatography, though such separation is unnecessary for the purposes of the present invention. The reaction producing compounds of the formulas IV and V is conducted utilizing an excess of the epihalogenhydrin, in the presence of either a catalytic quantity of an organic base such as piperidine, or an acid-binding agent such as, for example, sodium hydroxide or potassium carbonate. The reaction can be carried out in suitable solvents, such as alcohols, and may be accelerated by heating of the reaction mixture to a temperature in the range of 100° C.

Compounds of the formula VII, wherein $R_1$ and $R_2$ are as previously described in formula I and $R_7$ is benzyl, can be prepared from the 2-halogen-acetophenones of the formula

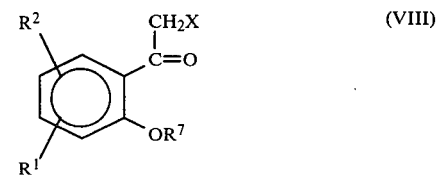

wherein $R_1$, $R_2$ and $R_7$ have the above-stated meaning, and X is selected from chlorine and bromine, by first reacting them with the alkali salt of a 2-dialkylphosphono acetic acid to form α-ketoacyl esters represented by the formula

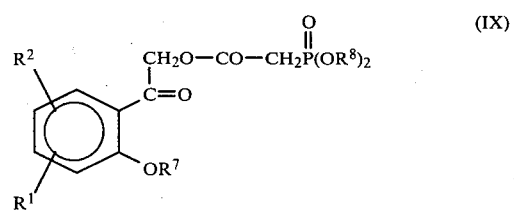

wherein $R_1$, $R_2$ and $R_7$ are as described with reference to formula VII above and $R_8$ is selected from methyl or ethyl. The compounds of formula IX are subsequently converted by intra molecular condensation to the 2,5-dihydro-furane-2-ones of formula VII. The starting compounds of formula VIII are generally available and may be prepared by known methods.

The compounds of the formula VII may be preferably prepared by reacting the acetophenones of formula VIII with the potassium salt of 2-diethyl-phosphono- acetic acid at room temperature. It is also possible to cyclize the α-ketoacyl esters of formula VIII either with potassium-tertiarybutylate in dimethoxane at low temperatures such as, for example, 0° to 10° C., for a period of time of about 1 hour. Alternatively, and more advantageously, the α-ketoacyl esters may be subjected to phase transfer catalysis in the presence, for example, of a compound selected from benzyltributylammonium bromide or tetrabutyl ammonium bromide, to form the butenolide.

The following examples are for illustrative purposes only and are not meant to limit or in any way redefine the inventions set forth in the broadcast claim of the application.

EXAMPLE 1

3-[-2-(2-hydroxy-3-tertiarybutyl amino-propoxy)-phenyl]-furane 2.7 grams of 3-(2-hydroxy-phenyl-furane were heated with 30 milliliters of epibromohydrin and catalytic quantities of piperidine, for 3 hours at a temperature of from 100° to 110° C. After concentration, the mixture of the epoxy-and the bromohydrin reaction products was separated by high pressure liquid chromatography. After evaporation of the solvents, 3 grams of 3-[2-(2,3-epoxy-propoxy)-phenyl]-furane were obtained in the form of an oil. The oil was then dissolved in 25 milliliters of methanol and 20 milliliters of tertiary butyl amine was added thereto, and the resulting mixture was then stirred for 2 days at room temperature. The mixture was then concentrated such as by solvent evaporation, the residue was taken up in methylene chloride and extracted with 0.1 normal HCl, and the aqueous phase was neutralized with sodium hydrogen carbonate.

The mixture was extracted a second time with methylene chloride, after which the organic phase was dried over sodium sulfate and concentrated. The resulting reaction product was then dissolved in toluene with the addition of a small amount of ethanol, and this solution was mixed with ethanolic HCl, to cause the hydrochloride salt of the above-entitled aryl-substituted furane to crystallize out slowly. Yield: 2.0 grams aryl-substituted furane as hydrochloride. M.P.: 150°-153° C.

EXAMPLES 2-11

In a manner analogous to Example 1, the compounds set forth in Table 1, below were prepared, and melting points were noted.

TABLE 1

| Example No. | $R^1$ | $R^2$ | $R^3$ | $R^4$ | $R^5$ | M.p. °C. | Salt |
|---|---|---|---|---|---|---|---|
| 2 | H | H | $CH_3$ | H | H | 122–123 | HCl |
| 3 | 4-$CH_3$ | H | $CH_3$ | $CH_3$ | H | 148–151 | HCl |
| 4 | 4-n-$C_3H_7$ | H | $CH_3$ | $CH_3$ | H | 195–196 | Oxalate |
| 5 | H | 5-n-$C_3H_7$ | $CH_3$ | $CH_3$ | H | 169–172 | HCl |
| 6 | 4-$CH_3$ | 5-$CH_3$ | $CH_3$ | $CH_3$ | H | 210–212 | HCl |
| 7 | 4-Cl | H | $CH_3$ | $CH_3$ | H | 190–193 | HCl |
| 8 | H | 5-$NHCOCH_3$ | $CH_3$ | $CH_3$ | H | 209–210 | HCl |
| 9 | H | H | H | H | 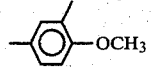 | 182–184 | HCl |
| 10 | H | H | H | H | —$NHCOCH_3$ | 160–162 | Fumarate |
| 11 | H | H | H | H | —$NHCOCH_3H_7^i$ (isopropyl) | 128–130 | HCl |

EXAMPLE 12

3-(2-hydroxy-phenyl)-furane

A. A solution of 39.9 gram (0.15 mole) 4-(2-benzyloxyphenyl)-2,5-dihydro-furane-2-one in 400 ml. tetrahydrofurane was prepared. The solution was placed in a nitrogen atmosphere and was held at a temperature of −60° C. while a 20% solution of di-isobutyl aluminum hydride (DIBAH) in toluene (250 ml.) was added in a dropwise manner. The reaction mixture was stirred at −60° C. for an additional 30 minutes, after which the excess DIBAH was decomposed by the addition of 100 ml. of 6N HCl to the mixture. The mixture was then poured over about 5 liters of ice water, and was extracted with chloroform. After evaporation of the solvent, the furane was obtained in a crude yield of 32.5 grams. The crude reaction product was then filtered through a silica gel column and further solvent was evaporated, whereby 24.8 grams crystalline 3-(2-benzyloxyphenyl)-furane was obtained.

M.P. 56°–58° C.

B. The benzylether prepared by the procedure outlined in sub paragraph A above was converted to the hydrophenyl furane and follows: 10.2 grams 3-(2-benzyloxyphenyl)-furane was placed in 50 ml. of a 1:1 solution of methanol/acetic ester, and was hydrogenated with hydrogen in the presence of 1.5 gram 10% palladium carbon, at room temperature and slight pressure. After absorption of one equivalent of hydrogen, the catalyst was filtered off and the solvent carefully drawn off at 20° C. An intensely colored, unstable substance remained, which was identified by its NMR spectrum as the desired phenol.

EXAMPLES 13-18

In a manner analogous to Example 12, compounds having the general structural formula shown below and substituted as set forth in Table 2, were prepared and their melting points were noted.

TABLE 2

[Structure: phenyl with R², R¹ substituents, O—CH₂C₆H₅, furanone ring]

| Example No. | R¹ | R² | M.p. °C. |
|---|---|---|---|
| 13 | 4-CH₃ | H | 59–60° C. |
| 14 | 4-Cl | H | 70–71 |
| 15 | 4-n-C₃H₇ | H | Oil |
| 16 | H | 5-n-C₃H₇ | 52–53 |
| 17 | H | 5-NHCOCH₃ | 184–186 |
| 18 | 4-CH₃ | 5-CH₃ | 82–83 |

EXAMPLE 19

4-(2-benzyloxy-phenyl)-2,5-dihydrofurane-2-one

A solution of 160 grams (0.524 mole) 2-benzyloxyphenacyl bromide in 500 milliliters acetonitrile was stirred with 147.3 grams (0.63 mole) of the potassium salt of 2-diethylphosphono-acetic acid for 15 hours at room temperature. The potassium bromide formed by the reaction was suction-filtered and the solvent removed. The reaction product was taken up in methylene chloride, extracted with water and concentrated under vacuum. 220 grams of crude α-ketol-phosphono-acetic ester was obtained which was admixed without further purification in one liter of 1,2-dimethoxyethane with 65 grams potassiumtertiary butylate at a temperature of 0° to 10° C. The reaction was completed after about 1 hour. This further reaction product was acidulated with dilute HCl, and then poured over water, and the organic phase was then separated. After evaporation of the solvent, 200 grams of the butenolide remained as an oil which became crystalline after trituration with ether, and yielded 81.4 grams of 4-(2-benzyloxyphenyl)-2,5-dihydro-furane-2-one.
M.P. 102°–104° C.

EXAMPLE 20

4-(2-hydroxy-4-chlorophenyl)-2,5-dihydro-furane-2-one

Like Example 19, this example relates to the preparation of compounds of the formula VII and illustrates additional processing techniques.

A. 76.7 grams (0.45 mole) 2-hydroxy-4-chloroacetophenone and 88.9 grams (0.52 mole) benzylbromide were dissolved in 500 milliliters ethanol and brought to a boil, at which point 29.6 grams (0.45 mole) KOH (85%) in about 1 liter ethanol, was added in dropwise fashion thereto. After 2 hours under reflux, the reaction mixture was subject to evaporation, and the residue was mixed with water and extracted with methylene chloride. The organic phase was extracted several times with 2 N NaOH, and then with water. After evaporation of the solvent, 100 grams of the benzylether was obtained as an oil, from which, after trituration with n-hexane, 75 grams of 2-benzyloxy-4-chloro-acetophenone having a M.P. of 64° C. crystallized out.

B. 68 grams (0.26 mole) 2-benzloxy-4-chloroacetophenone was dissolved in 700 milliliters of methanol, and 41.7 grams (0.26 mole) of bromine was added thereto in slow dropwise fashion under a temperature of from 0° to 10° C. The resulting mixture was stirred at room temperature for about 15 hours thereafter. Both the omega-bromoacetophenone and its corresponding ketal crystallized out. The ketal was then split by dissolving it in 300 milliliters of dioxane, and treating the solution with 300 milliliters of 6 N HCl for 1 hour at 40° C. This mixture was filtered, and 77.8 grams of 2-benzyloxy-4-chloro phenacyl bromide were obtained. M.P. 75°–78° C.

C. 40.5 grams (0.12 mole) of the phenacyl bromide obtained in paragraph B, above, was placed in solution in 400 milliliters of acetonitrile. 33.7 grams (0.145 mole) of the potassium salt of 2-diethylphosphono-acetic acid was added to the solution, and the resulting mixture was stirred for 15 hours at room temperature. Thereafter, the potassium bromide reaction by-product was suction-filtered, and the solvent was removed from the reaction mixture. The residue of the reaction mixture was taken up in methylene chloride, and was then extracted with water and concentrated under vacuum. 52.5 grams of crude α-ketol-phosphono-acetic ester was obtained, which crystallized after triturating with di-isopropylether.
Yield: 45.4 grams.
M.P.: 84°–85° C.

D. 45.4 grams (0.1 mole) of the above phosphonic ester were dissolved together with 3.25 grams (0.01 mole) tetrabutyl ammonium bromide in 350 milliliters methylene chloride and agitated vigorously in a two-phase reaction with 7.9 grams (0.12 mole) KOH (85%) in 250 milliliters water for one hour at 20° C. The organic phase was then washed with water until neutral and evaporated. The resultant residue was triturated with di-isopropyl ether, and 28 grams (4-(2-benzyloxy-4-chloro-phenyl)-2,5-dihydro-furane-2-one was obtained.
M.P.: 117°–122° C.

E. 17 grams of the above benzyl ether were combined with 80 milliliters 40% hydrogen bromide in glacial acetic acid, and the resulting mixture was stirred for one hour at room temperature. After evaporation, the residue was triturated with ether/di-isopropyl ether and suction-filtered.
Yield: 7.5 grams 4-(2-hydroxy-4-chloro-phenyl)-2,5-dihydro-furane-2-one.
M.P.: 184°–185° C.

EXAMPLES 21–25

In analogous manner to the procedures followed in Examples 19 and 20, compounds having the general structural formula shown below and substituted as set forth in Table 3, were prepared, and melting points where determined, were noted.

TABLE 3

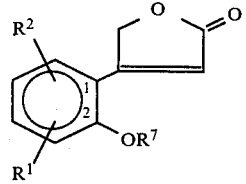

| Example No. | R¹ | R² | R⁷ | M.p. °C. |
|---|---|---|---|---|
| 21 | 4-CH₃ | H | —CH₂C₆H₅ | 94–99 |
| 22 | 4-n-C₃H₇ | H | —CH₂C₆H₅ | Oil |
| 23 | H | 5-n-C₃H₇ | —CH₂C₆H₅ | 99–102 |
| 24 | H | 5-NHCOCH₃ | —CH₂C₆H₅ | 204–205 |

TABLE 3-continued

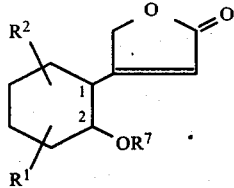

| Example No. | R¹ | R² | R⁷ | M.p. °C. |
|---|---|---|---|---|
| 25 | 4-CH₃ | 5-CH₃ | —CH₂C₆H₅ | 134-136 |

What I claim is:

1. A compound of the formula

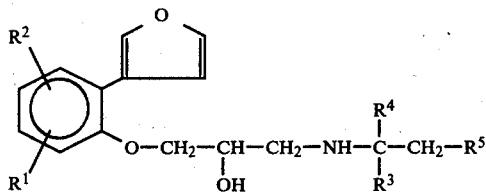

(I)

wherein $R_1$ and $R_2$ may be the same or different and are selected from hydrogen, halogen, alkyl groups and acylamino groups having 1 to 4 carbon atoms, $R_3$ and $R_4$ may be the same or different and are selected from hydrogen and methyl, $R_5$ is selected from hydrogen, dimethoxyphenyl and an acylamino group of the formula $R_6$—CONH— wherein $R_6$ is selected from alkyl having 1 to 4 carbon atoms and pharmaceutically acceptable acid addition salts thereof.

2. The compound of claim 1 selected from the group consisting of 3-[2-(2-hydroxy-3-tertiarybutylamino-propoxy)-phenyl]-furane, 3-[2-(2-hydroxy-3-iso-propylamino-propoxy)-phenyl]-furane, 3-[2-(2-hydroxy-3-tertiarybutylamino-propoxy)-4-methyl-phenyl]-furane, 3-[2-(2-hydroxy-3-tertiarybutylamino-propoxy)-5-methyl-phenyl]-furane, 3,[2-(2-hydroxy-3-tertiarybutylamino-propoxy)-4-(n-propyl)-phenyl]-furane, 3-[2-(2-hydroxy-3-tertiarybutylamino-propoxy)-5-(n-propyl)-phenyl]-furane, 3-[2-(2-hydroxy-3-tertiarybutylamino-propoxy)-4,5-dimethylphenyl]-furane, 3-[2-(2-hydroxy-3-tertiarybutylamino-propoxy)-4-chlorophenyl]-furane, 3-[2-(2-hydroxy-3-tertiarybutylamino-propoxy)-5-acetamidophenyl]-furane, 3-[2-(2-hydroxy-3-[3,4 dimethoxyphenyl]-ethylamino-propoxy)-phenyl]-furane, 3-[2-(2-hydroxy-3-acetamido-ethylamino-propoxy)-phenyl]-furane, and 3-[2-(2-hydroxy-3-isopropionamido-ethylamino-propoxy)-phenyl]-furane.

3. The compound of claim 1 wherein said salts are selected from the group consisting of maleinate, fumarate, oxalate, sulfate, hydrogen chloride and hydrogen bromide.

4. A composition comprising the compound of claim 1 in combination with a pharmaceutically acceptable carrier.

5. The composition of claim 4 wherein said carriers are selected from the group consisting of lactose, gelatin, cornstarch, stearic acid, ethanol, propylene glycol, ethers of tetrahydrofurfuryl alcohol, and water.

6. A method for lowering the blood pressure of a warm blooded animal comprising administering to said animal a therapeutically effective amount of the compound of claim 1.

7. The method of claim 5 wherein said therapeutically effective amount ranges from about 10 to about 200 milligrams per day in the instance where said compound is administered to a human being.

* * * * *

UNITED STATES PATENT AND TRADEMARK OFFICE
CERTIFICATE OF CORRECTION

PATENT NO. : 4,265,903
DATED : May 5, 1981
INVENTOR(S) : Erich Cohnen

It is certified that error appears in the above-identified patent and that said Letters Patent are hereby corrected as shown below:

IN THE TITLE, Cancel "FURNACES" insert -- FURANES --

IN THE ABSTRACT, lines 1, 14-15, 24, and 25, cancel "furnaces" -- furanes --

Column 1, line 1, cancel "FURNACES", insert -- FURANES --

Column 9, cancel the structural formula between lines 1 and 10.

Signed and Sealed this

Seventh Day of December 1982

[SEAL]

Attest:

Attesting Officer

GERALD J. MOSSINGHOFF

Commissioner of Patents and Trademarks